United States Patent [19]

Deckman et al.

[11] Patent Number: 5,395,979
[45] Date of Patent: Mar. 7, 1995

[54] METHOD FOR SEPARATING CATALYST FROM A HYDROFORMYLATION REACTION PRODUCT USING ALKYLATED LIGANDS

[75] Inventors: Harry W. Deckman, Clinton; Edward Kantner, East Brunswick; Joel R. Livingston, Jr., Basking Ridge; Michael G. Matturro, Lambertville; Edmund J. Mozeleski, Califon, all of N.J.

[73] Assignee: Exxon Chemical Patents Inc., Linden, N.J.

[21] Appl. No.: 23,235

[22] Filed: Feb. 25, 1993

[51] Int. Cl.$^6$ .................... C07C 45/50; C07C 45/78
[52] U.S. Cl. .................... 568/454; 568/451; 568/492
[58] Field of Search ............ 568/451, 454, 492; 502/20, 22, 24

[56] References Cited

U.S. PATENT DOCUMENTS

| | | | |
|---|---|---|---|
| 4,399,312 | 8/1983 | Russell et al. | 568/454 |
| 4,625,068 | 11/1986 | Young | 568/454 |
| 4,642,388 | 2/1987 | Young | 568/454 |
| 4,935,550 | 6/1990 | Miller et al. | 568/454 |
| 5,177,267 | 1/1993 | Morris et al. | 568/492 |
| 5,208,194 | 3/1993 | Pitchai et al. | 502/12 |
| 5,298,669 | 3/1994 | Healy et al. | 568/492 |

FOREIGN PATENT DOCUMENTS 8700881 11/1988 Netherlands ............ B01D 13/00

OTHER PUBLICATIONS

Imyanitov, et al., All–Union Scientific Research Institute of Petrochemical Processes, Neftekhimiya, 32, 3:200-7 (May–Jun. 1992).
Gosser et al., Reverse Osmosis in Homogeneous Catalysis, Journal of Molecular Catalysis, 2(1977) pp. 253–263.

Primary Examiner—Werren B. Lone
Attorney, Agent, or Firm—J. J. Mahon

[57] ABSTRACT

A catalyst for use in hydroformylation of olefins which comprises a Group VIII noble metal complexed with a phosphine ligand having at least one alkyl or aryl group bonded thereto, such as tris-4-propylphenyl phosphines and tris-4-octylphenyl phosphines. These and other triphenylphosphine catalysts can be separated from a crude reaction product of a noble metal-catalyzed hydroformylation reaction by contacting the crude reaction product with a dense polymeric, nonpolar membrane, preferably nonpolar polyolefin membranes.

40 Claims, 1 Drawing Sheet

METHOD FOR SEPARATING CATALYST FROM A HYDROFORMYLATION REACTION PRODUCT USING ALKYLATED LIGANDS

The present invention relates to a method for reducing the amount of a homogeneous, hydrocarbon soluble rhodium catalyst complex which permeates in the presence of CO, $H_2$ and ligands through a membrane when a membrane separation is used to separate hydroformylation reaction products, such as aldehydes and alcohols from the rhodium catalyst complex. In particular, the use of alkyl groups on phosphine ligands has been found to significantly improve rhodium retention especially when the catalyst is confined by a dense nonpolar polymeric membrane. Rhodium loss is decreased by performing the separation in an atmosphere containing CO and $H_2$ with partial pressures less than one atmosphere. In a preferred embodiment rhodium loss can be completely eliminated by using a dense nonpolar polymer membrane with phosphine ligands containing alkyl and/or alkylated aryl groups.

BACKGROUND OF THE INVENTION

Hydroformylation reactions involve the preparation of oxygenated organic compounds by the reaction of carbon monoxide and hydrogen (synthesis gas) with carbon compounds containing olefinic unsaturation. The reaction is typically performed in the presence of a carbonylation catalyst and results in the formation of compounds, for example, aldehydes, which have one or more carbon atoms in their molecular structure than the starting olefinic feedstock. In commercial operation, the aldehyde product is typically used as an intermediate which is converted by hydrogenation to an alcohol or by aldolization and hydrogenation to a higher alcohol. The aldol-hydrogenation route is used primarily for the manufacture of 2-ethylhexanol from propylene that is converted to n-butyraldehyde. The crude product of the hydroformylation reaction will contain a homogeneous catalyst, aldehydes, alcohols, unreacted olefin feed, synthesis gas and by-products, and in most cases, ligands. Homogeneous catalysts usable with the present invention are soluble in hydrocarbons or oils.

A variety of transition metal complexes catalyze the hydroformylation reaction, but only cobalt and rhodium carbonyl complexes are used in commercial plants. The reaction is highly exothermic; the heat release is approximately 125 kJ/mol (30 kcal/mol). The position of the formyl group in the aldehyde product depends upon the olefin type, the catalyst, the solvent, and the reaction conditions such as temperature and pressure. With several catalysts and reaction conditions, a predominantly straight chain product can be formed from a linear olefin feed.

Much research in the past twenty-five years has been directed to improving reaction selectivity to the linear product. The linear aldehydes which can be formed with rhodium catalyst complexes are intermediates for formulating biodegradable detergents, plasticizers, specialty polymers, etc. It has been found that with an unmodified cobalt catalyst (i.e., a catalyst having no ligand), the yield of a straight chain product is favored by very high CO partial pressures. Introduction of an organophosphine ligand to form an oil-soluble complex, e.g., $Co_2(CO)_6[P(n-C_4H_9)_3]_2$, can significantly improve the selectivity to the straight-chain alcohol under high pressure conditions. Rhodium catalysts containing selected complexing ligands, e.g., tertiary phosphines, can result in the predominant formation of the normal isomer with lower CO and $H_2$ partial pressures. In the most widely used commercial process for formation of linear aldehydes using a ligand-modified rhodium-catalyst, the reactor contains the rhodium complex catalyst, excess triphenylphosphine, CO, $H_2$ and a mixture of product aldehydes and condensation by-products. The product aldehyde, which is low in molecular weight and relatively volatile, may be recovered from the mixture by volatilization directly from the reactor or by distillation in a subsequent step. The catalyst either remains in or is recycled to the reactor. However, the complex catalyst and triphenylphosphine ligand are slowly deactivated and eventually the spent catalyst is removed for recovery of rhodium and reconversion to the active catalyst. This process, although effective for lower molecular weight aldehyde production, is not favored for higher molecular weight aldehydes which are higher boiling. Distillation temperatures needed for high boiling aldehyde recovery can cause catalyst deactivation to be accelerated.

Unfortunately, the low pressure rhodium catalyst systems that have been used commercially for the hydroformylation of propylene feedstocks to produce butyraldehyde cannot normally be used in industrial processes to make higher aldehydes because conventional separation technologies cannot remove the product aldehydes from the homogeneous rhodium catalyst complexes without significant destruction or rhodium loss. It is an object of this invention to overcome this limitation imposed by conventional separation technologies. Overcoming these limitations is particularly important for rhodium-based catalysts because of the high cost of rhodium metal.

Homogeneous ligated rhodium catalyst complexes can be formed with a variety of organophosphines in the presence of carbon monoxide and hydrogen. A typical homogeneous rhodium catalyst complex is formed with triphenylphosphine ligands in the presence of carbon monoxide and hydrogen. Under optimal conditions homogeneous rhodium catalyst complexes formed with triphenylphosphine, CO and $H_2$ have been reported to convert linear olefins into linear aldehyde products with less than approximately 1% isomerization under the most optimal conditions and approximately 5% isomerization under more practical conditions. The rhodium bonds to the triphenylphosphine ligand through a phosphorous atom. A schematic diagram of the triphenylphosphine ligand is set forth below:

A large number of complexes are formed between rhodium, triphenylphosphine, hydrogen, and carbon monoxide, because they form loosely bound molecular species which are involved in multiple equilibria as they dissociate and recombine with ligands in solution. Some of the reaction pathways in these multiple equilibria are set forth below:

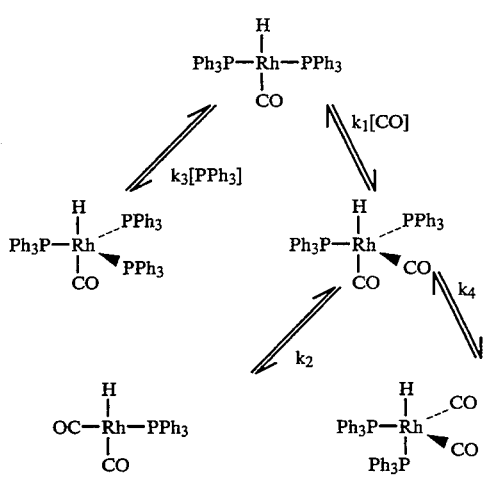

At least one of the complexes in this multiple equilibria can be a very active catalyst for the hydroformylation reaction which converts linear olefins into the next higher carbon number linear aldehydes by the addition of carbon monoxide and hydrogen. In addition, the catalyst causes some of the product aldehyde to react to dimer and trimer condensation products. The isomerization activity of the catalyst is extremely undesirable in applications designed to produce long chain linear aldehydes. Linear aldehydes containing between 12 to 15 carbon atoms are readily hydrogenated to linear alcohols which are premium products for formulating biodegradable liquid detergents.

Separation of several types of homogeneous rhodium/organophosphine ligand complexes from high boiling aldehyde products has been previously attempted using conventional separation techniques such as distillation, and liquid/liquid extraction. Even in a carbon monoxide and hydrogen atmosphere, rhodium/organophosphine ligand complexes are unstable at the elevated temperatures used for vacuum distillation of long chain aldehydes. Liquid/liquid separations based on the phase behavior of water soluble catalysts have also been attempted. These separations have been tried in cases with high boiling reaction products where the olefin feed and reaction products are not very soluble in water. In such cases, it is often advantageous to add a surfactant to the aqueous medium to enhance phase contacting so as to improve catalytic rate and selectivity to the desired products. This type of process is called "Phase Transfer Catalysis." However, when the surfactant is added, some carry-over of the noble metal into the organic phase at the conclusion of the process often results. This and other types of catalyst loss have made it impractical to make high boiling products using aqueous catalyst in processes where the products are decanted from an aqueous catalyst solution.

A variety of membrane separation processes have also been tested for separating high boiling point products from an oil soluble catalyst complex. Attempts have been made to create large catalyst complexes which could be separated by ultrafiltration. In one case, high molecular weight phosphine ligands were used to form a homogeneous catalyst complex. High molecular weight polymeric phosphine ligands are synthesized by reacting polyvinylchloride, polychloroprene or brominated polystyrene with lithium diphenylphosphide at 20° C. to 25° C. These homogeneous catalysts containing bulky ligands are thought to be more easily separated from the reaction products by ultrafiltration. See Imyanitov et al., All-Union Scientific Research Institute of Petrochemical Processes, Neftekhimiya, 32, No. 3:200-7 (May-June 1992). The process described herein uses a smaller catalyst complex which is not attached to a polymeric backbone.

It has also been known to use membranes to separate water-soluble catalysts from an aqueous solution. An example is set forth in European Patent No. 0263953, published on Aug. 29, 1986 (assigned to Ruhrchemie Aktiengesellschaft), which discloses a process for separating rhodium complex compounds, which contain water-soluble organic phosphines as ligands, from aqueous solutions in which excess phosphine ligand and, if necessary, other components are also dissolved, is characterized by the fact that the aqueous solution is subjected to a membrane separation process. According to this process, volatile organic substances are separated from the solution prior to conducting the membrane separation process. A typical membrane for use in this process is a cellulose acetate membrane. This process will not work with the types of oil-soluble catalysts used in the present invention.

Another patent which utilizes cellulose acetate, silicone rubber, polyolefin or polyamide membranes in the separation of catalysts from high boiling by-products of the hydroformylation reaction is Great Britain Patent No. 1312076, granted on May 15, 1970. According to this patent the aldehydes produced during the hydroformylation process are continuously withdrawn as an overhead vapor stream. The liquid stream containing the heavy by-products with the catalyst is passed over a membrane wherein approximately 78–94.3% of the catalyst is retained and the heavy by-products permeated. This is an unacceptably low level of catalyst retention which is overcome by the process of the present invention. Also in the present invention, the aldehyde product is contacted with the membrane rather than withdrawn as an overhead vapor stream.

In like manner, Great Britain Patent No. 1432561, granted on Mar. 27, 1972, (assigned to Imperial Chemical Industries LTD.) discloses a process for the hydroformylation of olefins which comprises reacting an olefin at elevated temperature and pressure with CO and $H_2$ in the presence of a compound of a group VIII metal and a biphyllic ligand of a trivalent P, As or Sb to give a crude liquid hydroformylation product containing an aldehyde and/or an alcohol, separating the aldehyde and/or alcohol from the crude product and leaving a liquid, bringing the liquid after separation of the Group VIII metal compound and free from aldehyde and alcohol under reverse osmosis conditions into contact with one side of a silicone rubber semi-permeable membrane in which the polymer chains have been at least partly cross-linked by gamma radiation, whereby the liquid retained by the membrane contains a higher concentration of Group VIII metal compounds and/or biphyllic ligand than the original liquid. Reverse osmosis membranes are different in composition and separate by a different mechanism than the membranes used in the present invention.

In an article by Gosser et al., entitled "Reverse Osmosis in Homogeneous Catalysis," Journal of Molecular Catalysis, Vol. 2 (1977), pp. 253–263, a selectively permeable polyimide membrane was used to separate soluble transition metal complexes from reaction mixtures by reverse osmosis. For example, separation of cobalt and rhodium complexes from hydroformylation products of 1-pentene. That is, a solution of 0.50 g of RhH(CO)(PPh$_3$)$_3$ in 40 ml of benzene and 10 ml of 1-pentene was stirred at 50° C. with a CO/H$_2$ mixture at ca. 4 atm pressure until no further pressure drop occurred. The pentene was completely converted to aldehydes according to proton nmr analysis. The solution was permeated through a polyimide membrane under 68 atm nitrogen pressure. The permeate (4.5 g passed in 2 min.) showed only 9% of the original rhodium concentration by X-ray fluorescence. The permeation rate of rhodium as set forth above, i.e., 9%, is considered unacceptable. The rhodium catalyst should be retained in an amount of greater than 99.5% to be a commercially feasible process. The technique employed does not use the dense polymer membranes nor the operating conditions used in the present invention.

Another example of the use of membranes to separate metal catalysts from hydroformylation products is set forth in Dutch Patent No. 8700881, published on Nov. 1, 1988. The method disclosed therein relates to one which improves the efficiency of membrane separation of hydroformylation products from expensive organometallic catalyst containing reaction mixtures. In Dutch Patent No. 8700881 a polydimethylsiloxane membrane having a thickness of 7 microns applied to a Teflon ® support was used in the separation of a reaction mixture containing C$_9$–C$_{15}$ alcohols, a homogeneous catalyst system comprising an organometallic complex of a transition metal from Group VIII or VIIa or Va of the Periodic Table, e.g., a tricarbonyl-(triphenylphosphine) cobalt catalyst, and 40% low-viscosity lubricating oil (an antiswelling or de-swelling agent). At a flow of 133 kg/m$^2$-day, the cobalt contents in the feed, retentate, and permeate were 600, 910, and 18 ppm, versus 840, 1930, and 160 ppm, respectively, for a mixture without the deswelling agent. The ligands disclosed in Dutch Patent No. 8700881 are all organic soluble ligands, e.g., triphenylphosphine, tri-n-alkylphosphine or acetyl acetonate. Critical to the process of Dutch Patent No. 8700881 is the addition of a de-swelling agent to the reaction mixture which assists in the separation of the products from the reaction mixture. The present invention operates without the use of a de-swelling agent.

The present inventors have been examining whether rhodium separation from hydroformylation products can be performed with a membrane when the catalyst complexes are formed using hydrocarbon or oil soluble phosphine ligands in the presence of an atmospheric mixture of CO and H$_2$. They have discovered that alkylated phosphine ligands together with dense nonpolar polymeric membranes are capable of substantially retarding the rhodium loss during the separation of the rhodium catalyst from the hydroformylation reaction products. It was also discovered that triphenylphosphine ligands used in conjunction with a dense polymeric, nonpolar membrane also substantially retards rhodium catalyst loss, although not as well as alkylated phosphines. Optimum operating conditions for the present invention involve performing the separations in an atmosphere of CO and H$_2$ each with partial pressures less than one atmosphere.

The present invention also provides many additional advantages which shall become apparent as described below.

SUMMARY OF THE INVENTION

A catalyst for use in hydroformylation of olefins which comprises a Group VIII noble metal complexed with a phosphine ligand having at least one alkyl group bonded thereto, such as tris-p-propylphenyl phosphines and tris-p-octylphenyl phosphines and also alkyl or aralkyl phosphines such as trioctyl phosphine.

These and other trialkyl, aralkyl, or triarylphosphine catalysts can be separated from a crude reaction product of a noble metal-catalyzed hydroformylation reaction by contacting the crude reaction product with a dense polymeric, nonpolar membrane, preferably nonpolar polyolefin membranes. The contacting is preferably done in the presence of a CO and H$_2$ atmosphere. Preferred partial pressures of the CO and H$_2$ are less than one atmosphere. The separation is preferably performed at a temperature between 50° C. and 145° C.

Furthermore, the present invention includes a method for separating a noble metal catalyst from a crude reaction product of a noble metal-catalyzed hydroformylation reaction. The crude reaction product including a Group VIII noble metal-ligand complex catalyst, unreacted olefin feed and a hydroformylation reaction product, wherein the ligand of the Group VIII noble metal-ligand complex catalyst is an alkylated or arylated ligand. This method includes the steps of: contacting the crude reaction product with a membrane (e.g., a dense polymeric, nonpolar membrane) which is capable of allowing a substantial portion of the unreacted olefin feed and hydroformylation reaction product to pass through while retaining a substantial portion of the Group VIII noble metal-ligand complex catalyst; removing unreacted olefin feed and hydroformylation reaction product which passes through the membrane as permeate; and retaining the Group VIII noble metal-ligand complex catalyst as retentate. In a preferred embodiment the separation is performed with a CO and H$_2$ atmosphere present where the partial pressures of the CO and H$_2$ are each less than one atmosphere.

The novel catalyst and/or dense polymeric, nonpolar membrane is preferably used in a method for producing higher aldehydes and higher alcohols. This method includes the following steps: (a) hydroformylating an olefinic feedstock with synthesis gas in the presence of a Group VIII noble metal-ligand complex catalyst to form a crude reaction product comprised of an olefin feed, a hydroformylation reaction product and a Group VIII noble metal-ligand complex catalyst, the ligand of the Group VIII noble metal-ligand complex catalyst is an alkylated or arylated ligand; (b) optionally adjusting the temperature of the crude reaction product and the CO and H$_2$ pressure before feeding the crude reaction product to a membrane separator; (c) removing the Group VIII noble metal-ligand complex catalyst from the crude reaction product by feeding the crude reaction product to a membrane separator which comprises a membrane (e.g., a dense polymer, nonpolar membrane) capable of allowing a substantial portion of the hydroformylation reaction product and unreacted olefin feed to pass through while retaining a substantial portion of the Group VIII noble metal-ligand complex catalyst; (d) recovering the hydroformylation reaction product and the unreacted olefin feed as permeate; (e) retaining the Group VIII noble metal-ligand complex catalyst as retentate; and (f) recycling the retained Group VIII noble metal-ligand complex catalyst to hydroformylation step (a).

Other and further objects, advantages and features of the present invention will be understood by reference to the following specification in conjunction with the annexed drawings, wherein like parts have been given like numbers.

DESCRIPTION OF THE PREFERRED EMBODIMENTS

Figure 1:
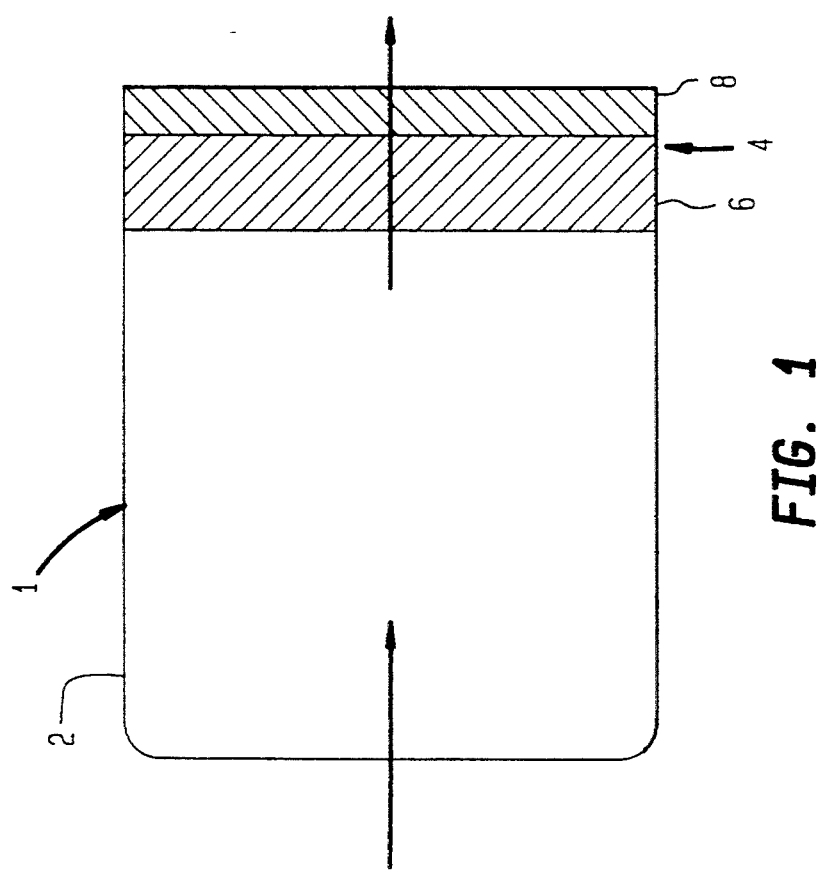
Fig. 1 is a schematic representation of a separation chamber having a permselective polymer membrane disposed therein.

Hydroformylation is a process of converting olefins to a product of one or more additional carbon numbers by the addition of carbon monoxide and hydrogen to the double bond(s) of the olefin in the presence of a catalyst at elevated temperatures and pressures. Recent developments of low pressure rhodium catalyst systems have been the subject of a considerable body of patent art and literature. Homogeneous rhodium-ligand catalyst complexes are able to take a linear terminal olefin and convert it into a predominantly linear aldehyde.

Linear $\alpha$-olefins are desirable feeds for rhodium hydroformylation processes because when carbon monoxide is added to the terminal position, the resulting linear aldehyde product can be hydrogenated to make primary linear alcohols which are used in the synthesis of biodegradable detergents. Substitution can occur at positions other than the end of the chain and the amount of non-terminal additions of carbon monoxide is determined by the ligand used to form the catalyst complex and the reaction conditions. In producing biodegradable detergents, it is desirable to have less than 15% substitution at sites other than the terminal position. With properly chosen phosphine ligands, the amount of addition at positions other than the terminal carbon can be as little as approximately 1%, when an oil soluble homogeneous rhodium catalyst complex is operated under optimal conditions such as with a 1000:1 molar excess of the ligand. However, for most phosphine ligands operated under more practical conditions the amount of non-terminal substitution is significantly greater and it can be as high as 60%.

A typical hydroformylation process using a homogeneous rhodium catalyst is shown schematically below:

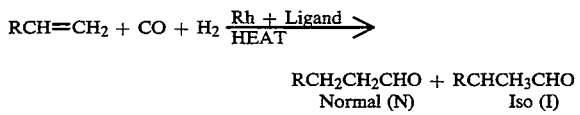

$$RCH=CH_2 + CO + H_2 \xrightarrow[\text{HEAT}]{\text{Rh + Ligand}}$$

$$\underset{\text{Normal (N)}}{RCH_2CH_2CHO} + \underset{\text{Iso (I)}}{RCHCH_3CHO}$$

At a temperature of 100° C. and a total CO and $H_2$ pressure of 12.75 kg (150 lbs.) the normal to iso ratio using rhodium as the catalyst may be below 1 or even as high as 100, depending on the ligand, ratio of ligand to rhodium, etc.

A ligand such as a phosphine can form a large number of different complexes with rhodium in the presence of carbon monoxide and hydrogen because these species form loosely bound, multiply coordinated complexes which are involved in multiple equilibria as they dissociate and recombine with ligands in solution. Some of these complexes act as homogeneous catalysts in the hydroformylation reaction which convert olefins to aldehydes by reaction with carbon monoxide and hydrogen while others involved in the multiple equilibria are not directly catalysts. We refer to all of these complexes as catalyst complexes because they transform back and forth as loosely bound ligands disassociate and recombine in solution.

Ligands used in the most preferred embodiment of the invention are capable of producing a normal to iso ratio greater than 5 with a linear $\alpha$-olefin feed. To maintain an active catalyst which produces such a normal to iso ratio, at least a 10:1 molar excess of the ligand compared to the rhodium concentration must be present in the crude hydroformylation product. Often a 100:1 molar excess of the ligand material is required.

In this invention the catalyst complex and product aldehyde in the crude hydroformylation product are separated with a membrane. The aldehyde product permeates the membrane while the catalyst does not permeate the membrane. This membrane separation may be performed at pressures and temperatures different from the reaction conditions. In this case the crude product is transferred from a hydroformylation reactor to a separate membrane module where the catalyst complex and product are separated. In the process of transferring the crude product from the reaction vessel CO and $H_2$ can be bled off to reduce the total pressure and the temperature can be raised or lowered. In a Organophosphine ligands which formed rhodium complexes that yielded the highest normal to iso ratio and lowest catalyst loss were alkylated triphenyl phosphines. Catalyst complexes were retained to a greater degree when the size of the ligand was increased by attaching alkyl groups, such as propyl and octyl, to the para position of the phenyl ring in a triphenylphosphine ligand. That is, nonpolar membranes allowed significantly less rhodium to permeate than polar membranes and also showed a decrease in the rhodium permeation as the size of the alkyl group on the phosphine ligand increased. With the addition of a large enough alkyl group to the ligand, nonpolar polyolefin membranes may completely confine rhodium complexes formed in the presence of a carbon monoxide and hydrogen atmosphere. For radiation crosslinked polyethylene membranes, a propyl group on the alkylphenyl phosphine ligand was sufficiently large to eliminate rhodium permeation through the membrane while a larger octyl group had to be incorporated into the ligand to stop rhodium complexes from passing through radiation crosslinked low density polyethylene membranes. In a preferred embodiment the invention is practiced with alkylated triphenyl phosphine ligands. preferred embodiment the CO and $H_2$ partial pressures are each less than one atmosphere and the crude hydroformylation product temperature is adjusted to be between 50° and 145° C. In a more preferred embodiment product temperature is adjusted to be between 75° and 100° C.

The present inventors have determined that satisfactory retention of certain rhodium-ligand catalytic complexes can occur when the crude hydroformylation product is separated with a dense polymeric nonpolar membrane. Ligands must be oil or hydrocarbon soluble organophosphines. Satisfactory separations have been achieved when the rhodium catalyst is combined with a triphenylphosphine ligand and particularly an alkylated triphenylphosphine ligand or a trialkylphosphine such as trioctyl phosphine. The large sized alkylated triphenylphosphine ligands and trialkyl phosphine ligands completely eliminated rhodium loss through the dense polymeric nonpolar membrane. That is, the present inventors have discovered that although organophosphine complexes of rhodium permeate most polymeric membranes, dense polymeric nonpolar membranes were more effective in confining the complexes and in some cases completely eliminated rhodium loss through the membrane.

ALKYLATED LIGANDS

The ligands are formed by alkylating the phenyl ring of a triphenylphosphine, particularly in the para position. In addition, the added alkyl group, especially when it is two or more carbons long, increases the bulk of the rhodium complex, aiding its separation from the product when using a size discriminating dense polymeric membrane.

Some examples of preferred alkylated ligands include tris-p-propylphenyl phosphine and tris-p-octylphenyl phosphine.

MEMBRANES

Preferred size discriminating dense nonpolar polymeric membranes may include polypropylene, low density polyethylene, and high density polyethylene. It is also preferred that the low density and high density polyethylene membranes be crosslinked by gamma irradiation to limit swelling and prevent melting.

As shown in FIGURE 1, the present invention includes a method for separating a noble metal catalyst from a crude reaction product of a noble metal-catalyzed hydroformylation reaction. The crude reaction product including a Group VIII noble metal-alkylated ligand complex catalyst, unreacted olefin feed, and a hydroformylation reaction product is contained within compartment 2 of a membrane separation device 1 which also contains a dense polymeric membrane 4 composed of a porous support 6 and a permselective nonpolar polymer membrane 8. Membrane 4 is capable of allowing a substantial portion of the unreacted olefin feed and hydroformylation reaction product to pass through while retaining a substantial portion of the Group VIII noble metal-ligand complex catalyst. Thereafter unreacted olefin feed and hydroformylation reaction product which passes through the membrane as permeate is removed for further downstream treatment and Group VIII noble metal-alkylated ligand complex catalyst is retained as a retentate and then recycled to the hydroformylation reaction.

There are many ways that one skilled in the art can incorporate the present catalyst separation method into an actual manufacturing process. Many of these involve feeding product from a hydroformylation reactor into a membrane separator. It is desirable to have the membrane separator operating at a lower CO and $H_2$ pressure than the hydroformylation reactor. Low pressures of CO and $H_2$ cannot be used in a hydroformylation reactor, therefore, the CO and $H_2$ gas pressure must be reduced when the hydroformylation product is transferred into the membrane separator. By running the membrane separator at low CO and $H_2$ partial pressures, rhodium retention can be significantly improved presumably due to an increase in the number of organophosphine ligands coordinating the Rh.

Hence it is desirable to have the membrane separation unit 1 operating at a pressure of one atmosphere to maximize the coordination of large ligands on the Rh. To accomplish this gas pressure would be bled down when product is transferred from a hydroformylation reactor into the membrane separation unit 1. Products permeating the membrane would be removed by a sweep liquid and the retentate containing the catalyst would be returned to the hydroformylation reactor. In a practical process the sweep liquid must be easily separable from aldehyde and alcohol products.

The present inventors examined via the below examples the ability of polymer membranes to confine complexes formed by the ligation of rhodium with substituted phosphines in the presence of carbon monoxide and hydrogen. Moreover, the below examples demonstrate how ligand size effects catalyst confinement by means of a membrane separator. The ligand size was increased by changing the para position about the phenyl ring of a triphenylphosphine ligand from hydrogen to either a methyl, propyl or octyl group. As the size of the ligand increased the catalytic rate in the hydroformylation reaction tended to decrease while the degree of substitution at non-terminal positions remained relatively low and constant.

EXAMPLE 1

A figure of merit for the ability to confine a rhodium complex is the percent rhodium loss factor which is the percent of rhodium catalyst transported across the membrane for a given volume of product (i.e., aldehyde) permeated through the membrane. It is believed that to be commercially viable this loss factor must be significantly lower than 1% for a reactor system which uses a membrane to separate the catalyst from the product.

To measure the percent rhodium loss factor, a linear $C_{10}$ aldehyde (i.e., decyl aldehyde) was chosen as a representative product and a catalytic amount (i.e., approximately 120 ppm) of the rhodium complex being studied was dissolved into the product along with a 100:1 molar excess of the ligand. Transport of this complex, aldehyde and ligand across selected polar and nonpolar polymeric membranes were measured using a glass diffusion cell apparatus. The rhodium complex was stabilized by bubbling a carbon monoxide and hydrogen mixture through each half cell at atmospheric pressure. The polymer membrane was clamped between two half cells using polytetrafluoroethylene (PTFE) coated Viton O-rings to achieve a leak-free seal. Each of the half cells was filled with approximately 165 ml of liquid and agitated with magnetic stir bars, and during the course of the experiment the liquid level in the half cells changed because of differential permeabilities of the aldehyde solution and heptamethylnonane sweep liquid. All experiments were conducted at approximately 100° C. which is well below the highest temperature that rhodium complexes can tolerate without significant thermally induced degradation. By operating at high temperatures, flux through the membrane is maximized.

A selected group of polar and nonpolar polymeric membranes were employed to study the rhodium/alkylated triphenylphosphine complexes according to the present invention. The nonpolar membranes were polyolefin materials such as polypropylene (PP), low density polyethylene (LDPE), and high density polyethylene (HDPE) which are set forth below in Table 1.

TABLE 1

| (NONPOLAR POLYOLEFIN MEMBRANES) | | | |
|---|---|---|---|
| Material | Crosslinking | Manufacturer | Thickness ($\mu$m) |
| PP | No | Chemplex | 7 |
| LDPE | 90 & 180 MRad. | Pall RAI | 23 |

TABLE 1-continued
(NONPOLAR POLYOLEFIN MEMBRANES)

| Material | Crosslinking | Manufacturer | Thickness (μm) |
| --- | --- | --- | --- |
| HDPE | 60 MRad. | Pall RAI | 27 |

Both the low density (LDPE) and high density (HDPE) polyethylene membranes shown in Table 1 were crosslinked by gamma irradiation. For both membrane materials, the molecular weight of the parent polyethylene material was between 50,000 and 100,000. For polyethylene the radiation chemistry of the polymer chain resulted in crosslinking with about 1 crosslinkage induced per 100 ev of ionizing radiation absorbed by the polymer. The HDPE material was irradiated with 60 megarad (M Rad) dosage resulting in a molecular weight of 7500 between radiation induced crosslinks. Dosages of 90 and 180 megarads were used to crosslink samples of the LDPE material which resulted in a molecular weight of 5000 and 2500, respectively, between crosslinks.

The other nonpolar membrane material listed in Table 1 is a 7 micron thick polypropylene membrane made by Chemplex Industries for use as an X-ray window. Tacticity of the propylene was not measured, however, it was expected that the manufacturing process used to make the membrane material produced a tactic polypropylene.

The polar membranes used in this study were polyureaurethane (PUU), polyethylene adipate/norbornene (PEA/norbornene), and polyethylene adipate/pyromellitic dianhydride/methylene-bis-o-chloroaniline (PEA200/PMDA/MOCA). A brief summary of their characteristics are given below in Table 2. All of the polar membranes listed in Table 2 were prepared by solution casting either on a release paper or onto a porous teflon (Gortex ®) membrane. Although none of the polar membranes tested were stabilized by crosslinking, they did not dissolve or excessively swell in aldehyde solutions at approximately 100° C. The limited amount of swelling that these membranes experienced was due to association of blocks (or segments) on the polymer backbone which tended to act like physical crosslinking sites.

TABLE 2
(POLAR MEMBRANES)

| Material | Crosslinking | Manufacturer | Thickness (μm) |
| --- | --- | --- | --- |
| PEA200/PMDA/MOCA | No | Exxon Chemical | 20 |
| PUU | No | Esso Pet. Can. | 23 |
| PEA/Norborene | No | Exxon Chemical | 20 |

The PEA200/PMDA/MOCA was made by casting a dimethylformamide (DMF) solution containing approximately 30% solids. The solids were comprised of 1 part polyethylene adipate (PEA) of 2000 mol. wt., 2 parts pyromellitic dianhydride (PMDA), and 1 part methylene-bis-o-chloroaniline (MOCA). The film was cast on 0.02 micron Gortex ® support (80% porous) and dried first under a nitrogen blanket at room ambient temperature overnight, then at 120° C. overnight, and finally at 260° C. for 5 minutes with a one hour heat-up time. The resulting film formed a 20 micron yellow layer on Gortex ®. Structures of the PEA2000, PMAD and MOCA components are shown schematically below:

MOCA: Methylene-bis-o-chloroaniline

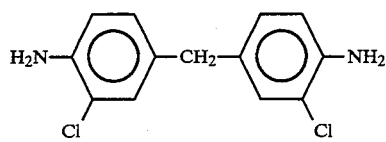

PMDA: Pyromellitic Dianhydride

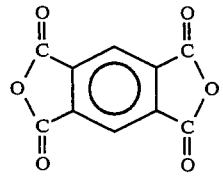

PEA Polyethylene Adipate (2000)

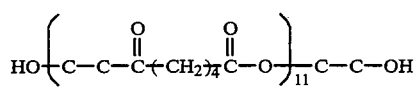

PUU was a polyureaurethane membrane made by Esso Petroleum Canada. The membrane was not chemically crosslinked, however, hard and soft segments in the polymer backbone have been shown to act as physical crosslinks limiting swelling to less than 75% in aromatic solvents at 100° C. The membrane was solution cast as a 23 μm thick film on release paper and was opaque and yellow colored in appearance. The chemical structure of PUU is diagrammed below:

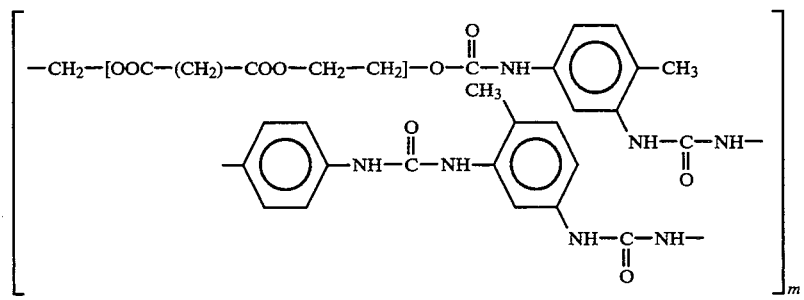

PEA/norbornene was also made by solution casting a mixture of polyethylene adipate (500 mol. wt.) and endomethylene tetrahydrophthalyl chloride in chloroform on a Gortex® support. The film was dried overnight under nitrogen and then baked successively at 100° C., 150° C., and 200° C., water washed at room ambient temperature for 3 hours, and finally dried at 100° C. for 10 hours. The resulting membrane was dark brown and opaque. The structure of the PEA/norbornene membrane is shown schematically below:

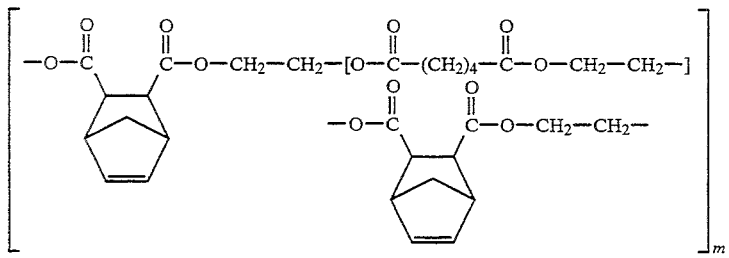

Rhodium complexes used in the permeation studies with the polar and nonpolar membranes were formed from a variety of oil soluble phosphine ligands. Table 3 summaries the oil soluble phosphine ligands used to complex the catalytic amounts (approximately 120 ppm) of rhodium. The rhodium complexes were formed using a 100:1 molar excess of the ligand in an aldehyde solution through which a mixture of carbon monoxide and hydrogen was bubbled at atmospheric pressure. The chemistry of rhodium complexes is known to be affected by trace impurities such as Fe and Cl⁻ and care was taken to use relatively pure sources of rhodium and ligand materials. Table 3 also summaries the catalytic properties of these complexes in converting 1-octene and atmospheric pressure carbon monoxide and hydrogen to an aldehyde at approximately 100° C. reaction temperature in a glass vessel. The initial rate of conversion of the linear α-olefin was used to compute the turnover frequency set forth in Table 3 which is the number of product aldehyde molecules made by each rhodium atom per second. Turnover frequencies shown in Table 3 are all greater than 1 per second which is a desirable turnover frequency for practical catalysis. For the homologous series of alkylated phenylphosphine ligands shown in Table 3 (i.e., triphenyl, tri-3-tolyl, tri-propyl-phenyl, and tri-octyl-phenyl), the turnover frequency decreases as the ligand size increases.

TABLE 3

| (PHOSPHINE LIGANDS AND REACTION PROPERTIES OF COMPLEXES) | | |
|---|---|---|
| Ligand Complex | Isomerization: Normal/Iso Ratio | Turnover Frequency Second$^{-1}$ |
| Tri-Octyl Phosphine | 2:1 | 4 |
| Triphenyl Phosphine | 7.5:1 | 11 |
| Tri-4-tolyl Phosphine | 6.5:1 | 7.5 |
| Tri-4-propyl-phenyl Phosphine | 6.5:1 | 5 |
| Tri-4-octyl-phenyl Phosphine | 6.5:1 | 3 |

Another measure of the catalyst performance listed in Table 3 is the normal/iso ratio which is the ratio of normal to branched aldehyde formed in the hydroformylation reaction. A normal/iso ratio of 6.5:1 corresponds to approximately 13% substitution at non-terminal positions in the hydroformylation reaction and is at the lower end of the acceptable range for formulating biodegradable detergents. The selectivity to the linear product can be improved by operating with a molar ligand excess greater than the 100:1 used in the experiments listed in Table 3. Thus, it is expected that the homologous series of alkylated phenylphosphine ligands shown in Table 3 can be used as ligands for hydroformylating aldehyde products needed to make biodegradable detergents.

Transport of small amounts of the 0.001 molar (approximately 120 ppm) concentration of rhodium out of the aldehyde product into the sweep was assayed by inductively coupled plasma emission spectroscopy which is an analytical method commonly used to detect trace metals. Inductively coupled plasma emission spectroscopy has an absolute detection limit of 9 parts per billion of rhodium. In this experiment sample preparation entailed a dilution factor of 1 to 5, and consequently, the test samples had a detection limit ranging from 0.009 to 0.045 parts per million of rhodium.

To measure the flux of the aldehyde, phosphine ligand and heptamethylnonane, small liquid test samples (approximately 0.2 ml) were periodically removed from each side of the diffusion cells and analyzed to determine time varying compositions in each half cell. Analyses were done on a HP5890A gas chromatograph equipped with an FID detector. Separation of molecular species was accomplished using a 30 meter nonpolar glass capillary column employing a temperature profile designed to yield clean component separations while minimizing analysis time. The percent area in the gas chromatograph trace (concentration) of each feed component was plotted as a function of time for each component. The compositions in each half cell for all components were found to vary linearly with time when less than approximately 25% of the molecules had permeated the membrane. This behavior was as would be expected in the initial phase of this type of diffusion experiment when the swelling state in the membrane does not change with time. From the slope of the linear increase in concentration with time, the flux at unit activity for permeation of each individual component, i.e., into or out of a half cell was computed from:

$$\text{Flux}^i = \frac{(\text{Slope}^i)\, V_{half\,cell}\, \rho_{half\,cell}\, t_{membrane}\, (1 - a^i_{half\,cell})}{100 f^i_{half\,cell}\, GC^i_{response}\, A_{membrane}}$$

where $V_{half\,cell}$ = volume of liquid in half cell receiving permeate of approximately 165 cc;

$\rho_{half\,cell}$ = average density in half cell receiving permeate;

$f^i_{half\,cell}$ = wt. fraction of component (i), in half cell from which permeate leaves;

$GC^i_{response}$ = gas chromatograph response for component (i);

$Slope^i$ = % GC (area)/hour for component (i);

$A_{membrane}$ = active membrane area of approximately 7.07 cm²;

$t_{membrane}$ = membrane thickness; and $a^i_{half cell}$ = correction factor due to change of volume with time in the half cell.

The above equation can be used to compute the flux of a component both from the rate at which it leaves the half cell into which it was filled and from the rate at which it arrives in the opposite half cell. This provides two separate measurements of the flux of an individual component.

Therefore, the percentage of phosphine ligand lost through the membrane from each volume of aldehyde permeated can be calculated using the formula given below:

% Loss of Ligand = $(Flux^{TPP}/Flux^{Aldehyde})$(% TPP in Aldehyde Feed)

The amount of rhodium lost from the permeate side was computed from inductively coupled plasma emission spectroscopy measurements of rhodium concentrations in the starting aldehyde feed and the heptamethylnonane sweep at the end of the run. The formula used to determine the percent of rhodium (Rh) lost through the membrane for each volume of aldehyde permeated is:

Loss of Rh = (Rh Concentration in Sweep/Rh Concentration in Feed)(% of Aldehyde Transferred from Sweep to Feed)

This study examined the ability of polymer membranes to confine rhodium complexes formed with large phosphine ligands in the presence of an atmospheric pressure of carbon monoxide and hydrogen. Under atmospheric pressure with a large 100:1 molar excess of the phosphine ligand, the multiple equilibria between rhodium ligation states will shift to form a predominantly triply ligated complex. The triply ligated complex is significantly larger than complexes with one or two phosphine ligands attached. To the extent that the distribution of complexes in the membrane is similar to that in solution, the use of atmospheric carbon monoxide and hydrogen is expected to aid in confining the rhodium complexes by forming more of the larger triply ligated species. The size of the rhodium complex is also determined by the molar excess of the ligand and the nature of the R group (e.g., phenyl, alkylphenyl, phenylalkyl, and alkyl) attached to the phosphorous in the ligand. The results of the studies examining confinement of rhodium complexes formed with tris-4-propylphenyl phosphine ligands are summarized in Table 4 below. It is seen that the percent rhodium loss was significantly larger for polar membranes than for nonpolar membranes. Rhodium losses for the polar membranes ranged from 2.5 to 4.1% while nonpolar polyolefin membranes had a maximum loss of 0.7% and a minimum loss of less than 0 1%. In fact no rhodium was detected in the permeate for the experiments which obtained the minimum rhodium loss and the 0.1% rhodium loss reported in Table 4 is a detectability limit. Complete confinement of rhodium/tris-4-propylphenyl phosphine complexes was obtained with a crosslinked high density polyethylene membrane.

TABLE 4

(PERFORMANCE OF MEMBRANES WITH TRI-4-PROPYLPHENYL PHOSPHINE LIGAND)

| Membrane | Membrane Polarity | Ligand Loss % | Aldehyde Flux Kg-μm/ (m²-Day) | % Rh Loss |
|---|---|---|---|---|
| PEA500/Norborene | Polar | <0.1 | <10 | Not Checked |
| PEA2000/PMDA/MOCA | Polar | <0.1/<0.1 | 44/52 | 4.1/3.5 |
| PUU | Polar | 5.5/8 | 264/368 | 2.5/2.6 |
| HDPE (180 MRAD) | Nonpolar | <0.1/<0.1 | 121/132 | <0.1/<0.1 |
| LDPE (90 MRAD) | Nonpolar | 0.5 | 300 | 0.7 |
| LDPE (180 MRAD) | Nonpolar | — | 250 | 0.5 |

To determine if the rhodium loss or any other permeation property of the membranes changed with time, many experiments were repeated using the same membrane. Experiments which were re-run with the same membrane are recorded as two numbers separated by a slash mark in Table 4 above. It is seen that relatively small changes occurred between sequential. 100 to 200 hour long runs with the same membrane and that the high density polyethylene (HDPE) membrane completely confined both the ligand and rhodium complex in both runs (i.e., the detection limit corresponds to a loss of less than 0.01%).

The amount of ligand permeation through the membrane (i.e., % ligand loss) tracks the amount of rhodium loss for all membranes except for the PEA2000/PMDA/MOCA. To determine how ligand size affected ligand and rhodium complex loss, the permeation characteristics of complexes formed from a homologous series of alkylphenyl phosphines were studied. Table 5 summarizes permeation characteristics of rhodium complexes formed with alkylphenyl phosphines through polar polyureaurethane (PUU) membranes, Table 6 summarizes results for nonpolar radiation crosslinked low density polyethylene (LDPE) membranes, and Table 7 summarizes results for nonpolar radiation crosslinked high density polyethylene (HDPE) membranes. It is seen that for both membrane types, the ligand and rhodium loss decrease systematically with increasing ligand size, indicating that size effects play an important role in rhodium complex and ligand confinement. For a fixed ligand size, the nonpolar LDPE membrane always confined the complex and ligand more effectively than the polar PUU membrane, indicating that differences in confinement between polar and nonpolar membranes extend over several ligand sizes. For the LDPE membrane, the loss of the rhodium complex fell below the detectability limit when the alkyl group was octyl. This is a larger radical (R) group than was required to confine complexes with the HDPE membrane where no permeation was detected with a propyl group. The difference in the size of the R group required to confine the ligand and complex with LDPE and HDPE membranes supports the idea that polymer chain packing affects permeation characteristics.

TABLE 5

(Permeation using Alkylphenyl Phosphine Ligands and PUU Membranes)

| Ligand | % Ligand Loss | C₁₀ Aldehyde Flux Kg-μm/(m²-Day) | % Rh Loss |
|---|---|---|---|
| Triphenyl Phosphine | 55 | 250 | 7.5 |

TABLE 5-continued
(Permeation using Alkylphenyl Phosphine Ligands and PUU Membranes)

| Ligand | % Ligand Loss | $C_{10}$ Aldehyde Flux Kg-μm/(m²-Day) | % Rh Loss |
|---|---|---|---|
| Tri-4-tolyl Phosphine | 18/19 | 172/231 | 4.1/3/6 |
| Tri-4-propylphenyl Phosphine | 5.5/8 | 264/368 | 2.5/3.6 |

TABLE 6
(Permeation with 90 MRad Crosslinked Low Density Polyethylene Membranes)

| Ligand | % Ligand Loss | $C_{10}$ Aldehyde Flux Kg-μm/(m²-Day) | % Rh Loss |
|---|---|---|---|
| Triphenyl Phosphine | 1.2 | 200 | 2 |
| Tri-4-propyl phenyl Phosphine | 0.5 | 300 | 0.7 |
| Tri-4-octylphenyl Phosphine | — | 175 | <<0.1 |

TABLE 7
(Permeation with 60 MRad Crosslinked High Density Polyethylene Membranes)

| Ligand | % Ligand Loss | $C_{10}$ Aldehyde Flux Kg-μm/(m²-Day) | % Rh Loss |
|---|---|---|---|
| Triphenyl Phosphine | — | 220 | 3.8 |
| Tri-4-propylphenyl Phosphine | — | 126 | <0.1 |

Tables 4, 5, 6 and 7 have summarized the ability of selected polar and nonpolar membranes to confine different sized alkylphenyl phosphine ligands and rhodium complexes. Rhodium complexes formed from alkylphenyl phosphine ligands can produce aldehyde products with relatively high normal/iso ratios from linear a-olefins. The turnover frequency and normal is iso ratios obtained with rhodium complexes made with alkylphenyl phosphine ligands under non-optimal catalytic conditions using atmospheric pressure carbon monoxide and hydrogen with a 100:1 molar ligand excess are summarized above in Table 3.

Confinement of rhodium complexes formed with two other ligands by polyureaurethane membranes are given in Table 8 below. It is seen that the polar polyureaurethane membrane was able to completely confine one of the complexes which was formed using a relatively nonpolar ligand having only an octyl group attached to the phosphorous. Complexes formed from this tri-octyl phosphine ligand do not give a high normal to iso ratio in aldehyde products from the hydroformylation reaction.

TABLE 8
(Permeation of Other Ligands and PUU Membranes)

| Ligand | % Ligand Loss | $C_{10}$ Aldehyde Flux Kg-μm/(m²-Day) | % Rh Loss |
|---|---|---|---|
| Triphenylpropyl Phosphine | <0.1 | 266/301 | 7.7/10 |
| Tri-octyl Phosphine | <0.1 | 109 | <0.07 |

The present inventors have discovered that rhodium complexes formed with alkylphenyl phosphine ligands can be confined by nonpolar polyolefin membranes blanketed by atmospheric pressure carbon monoxide and hydrogen. The size of the alkyl group needed to prevent the permeation of the rhodium complex depends on the packing of the polymer chains in the membrane with low density polyethylene requiring a longer alkyl chain than higher density polyethylene.

EXAMPLE 2

To isolate size exclusion effects from other physical interactions such as alteration of the ligand coordination by solubilization from dipolar interactions with the polymer or dissociation of the complex into ionic species, representative types of polar, nonpolar and ion exchange membranes were selected for testing. The nonpolar membranes were low density polyethylene (LDPE) and polypropylene(PP). The ion exchange membranes were a cationic exchange membrane and an anionic exchange membrane sold by Ionac. The polar membranes were a polyureaurethane membrane (PUU), polyethylene adipate/pyromellitic dianhydride/methylene-bis-o-chloroaniline (PEA2000/PMDA/MOCA) membrane, polyethylene adipate/pyromellitic dianhydride/methylene-bis-o-chloroaniline (PEA3000/PMDA/MOCA) membrane, polysulfone membrane, and polycarbonate membrane.

All permeation experiments were carried out with either a linear $C_{10}$ or $C_{13}$ aldehyde mixed with a rhodium/triphenylphosphine (TPP) ligand complex in one half cell and a branched $C_{16}$ (heptamethylnonane) hydrocarbon sweep in the other. Most experiments were run with a TPP to rhodium ratio of 100.

To measure the flux of the aldehyde, TPP ligand, and heptamethylnonane, small liquid test samples (approximately 0.2 ml) were periodically removed from each side of the diffusion cell and analyzed to determine time varying compositions in each half cells. Table 9 below demonstrates the flux through the membranes tested hereunder.

TABLE 9
(TPP Ligand Permeation through Various Membranes)

| Membrane | Temp. °C. | Aldehyde Flux Kg-μm/(m²-Day) $C^{10}$ | Aldehyde Flux Kg-μm/(m²-Day) $C^{16}$ | % Rh Loss |
|---|---|---|---|---|
| PUU | 100 | 200 | 40 | 7.5 |
| PEA2000/PMDA/MOCA | 25 | <10 | <10 | No Data |
| PEA3000/PMDA/MOCA | 100 | 130 | 15 | 10.8 |
| Polysulfone | 100 | <10 | <10 | No Data |
| Polycarbonate | 100 | <10 | <10 | No Data |
| Anionic | 100 | 3.5 | 3 | 15 |
| Cationic | 100 | 9.5 | 9 | 35 |
| Polypropylene | 100 | 168 | 182 | 2.8 |
| LDPE | 100 | 198 | 277 | 2 |

Although the flux rates in the PUU and PEA3000/PMDA/MOCA were acceptable the percent rhodium loss was too high. The flux rate in the other polar membranes was less than 10 kg-μm/m²-day which is too low to permit an accurate determination of the rhodium loss. The ion exchange membranes showed no selectivity for the transport of aldehydes compared to the saturated heptamethylnonane sweep; however, their rhodium loss was less than 100% implying some selectivity of rhodium confinement. The smallest rhodium losses were observed with the nonpolar membranes tested. The nonpolar polyolefin membranes had the highest aldehyde fluxes and provided the greatest restriction for transport of the rhodium catalyst/ligand complex.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A method for separating a noble metal catalyst from a crude reaction product of a noble metal-catalyzed hydroformylation reaction, said crude reaction product including a Group VIII noble metal-ligand complex catalyst, unreacted olefin feed and a hydroformylation reaction product, said ligand of the Group VIII noble metal-ligand complex catalyst is an alkylated or arylated ligand, wherein the method comprises: (a) contacting said crude reaction product with a membrane capable of allowing a substantial portion of said unreacted olefin feed and hydroformylation reaction product to pass therethrough while retaining a substantial portion of said Group VIII noble metal-ligand complex catalyst; (b) removing unreacted olefin feed and said hydroformylation reaction product which passes through said membrane as permeate; and (c) retaining said Group VIII noble metal-ligand complex catalyst as retentate.

2. The method according to claim 1 wherein said alkylated or arylated ligand is a phosphine ligand with at least one alkyl group bonded thereto.

3. The method according to claim 2 wherein said phosphine ligand is triphenyl phosphine.

4. The method according to claim 3 wherein the aryl group is alkylated and said alkyl group comprises between about 2 to about 8 carbons.

5. The method according to claim 4 wherein said alkyl group is bonded to the para position about said triphenyl phosphine.

6. The method according to claim 1 wherein said Group VIII noble metal catalyst is rhodium.

7. The method according to claim 1 wherein said membrane is a dense polymeric membrane.

8. The method according to claim 7 wherein said dense polymeric membrane is nonpolar.

9. The method according to claim 8 wherein the nonpolar membrane is a nonpolar polyolefin membrane.

10. The method according to claim 9 wherein said nonpolar polyolefin membrane is selected from the group consisting of: polypropylene membranes, crosslinked low density polyethylene membranes and crosslinked high density polyethylene membranes.

11. The method according to claim 1 wherein the separation is conducted in a carbon monoxide and hydrogen containing atmosphere where the partial pressures of the carbon monoxide and hydrogen are less than one atmosphere.

12. The method according to claim 1 wherein the separation is conducted at a temperature in the range between about 50° C. to about 145° C.

13. A method for producing higher aldehydes and higher alcohols which comprises:

(a) hydroformylating an olefinic feedstock with synthesis gas in the presence of a Group VIII noble metal-ligand complex catalyst to form a crude reaction product comprised of an olefin feed, a hydroformylation reaction product and a Group VIII noble metal-ligand complex catalyst, said ligand of the Group VIII noble metal-ligand complex catalyst is an alkylated or arylated ligand;

(b) removing said Group VIII noble metal-ligand complex catalyst from said crude reaction product by feeding said crude reaction product to a membrane separator which comprises a membrane capable of allowing a substantial portion of said hydroformylation reaction product and unreacted olefin feed to pass therethrough while retaining a substantial portion of said Group VIII noble metal-ligand complex catalyst;

(c) recovering said hydroformylation reaction product and said unreacted olefin feed as permeate;

(d) retaining said Group VIII noble metal-ligand complex catalyst as retentate; and (e) recycling the retained Group VIII noble metal-ligand complex catalyst to said hydroformylation step (a).

14. The method according to claim 13 wherein the separation is conducted in a carbon monoxide and hydrogen containing atmosphere where the partial pressures of the carbon monoxide and hydrogen are less than one atmosphere.

15. The method according to claim 13 wherein the separation is conducted at a temperature in the range between about 50° C. to about 145° C.

16. The method according to claim 13 wherein said alkylated or arylated ligand is a phosphine ligand with at least one alkyl group bonded thereto.

17. The method according to claim 16 wherein said phosphine ligand is triphenyl phosphine.

18. The method according to claim 17 wherein said alkyl group comprises between about 2 to about 8 carbons.

19. The method according to claim 18 wherein said alkyl group is bonded to the para position about said triphenyl phosphine.

20. The method according to claim 13 wherein said Group VIII noble metal catalyst is rhodium.

21. The method according to claim 13 wherein said membrane is a dense polymeric membrane.

22. The method according to claim 21 wherein said dense polymeric membrane is nonpolar.

23. The method according to claim 22 wherein the nonpolar membrane is a nonpolar polyolefin membrane.

24. The method according to claim 23 wherein said nonpolar polyolefin membrane is selected from the group consisting of: polypropylene membranes, crosslinked low density polyethylene membranes and crosslinked high density polyethylene membranes.

25. A catalyst for use in hydroformylation of olefins which comprises a Group VIII noble metal-ligand complex wherein said ligand is an alkylated or arylated ligand.

26. The catalyst according to claim 25 wherein said alkylated or arylated ligand is a phosphine ligand with at least one alkyl group bonded thereto.

27. The catalyst according to claim 26 wherein said phosphine ligand is triphenyl phosphine.

28. The catalyst according to claim 27 wherein said alkyl group comprises between about 2 to about 8 carbons.

29. The catalyst according to claim 28 wherein said alkyl group is bonded to the para position about said triphenyl phosphine.

30. The catalyst according to claim 25 wherein said Group VIII noble metal catalyst is rhodium.

31. A method for separating a noble metal catalyst from a crude reaction product of a noble metal-catalyzed hydroformylation reaction, said crude reaction product including a Group VIII noble metal-ligand complex catalyst, unreacted olefin feed and a hydroformylation reaction product, wherein the method comprises: (a) contacting said crude reaction product with a dense polymeric, nonpolar membrane capable of allowing a substantial portion of said unreacted olefin feed and hydroformylation reaction product to pass therethrough while retaining a substantial portion of said Group VIII noble metal-ligand complex catalyst; (b) removing unreacted olefin feed and said hydroformylation reaction product which passes through said membrane as permeate; and (c) retaining said Group VIII noble metal-ligand complex catalyst as retentate.

32. The method according to claim 31 wherein the nonpolar membrane is a nonpolar polyolefin membrane.

33. The method according to claim 32 wherein said nonpolar polyolefin membrane is selected from the group consisting of: polypropylene membranes, crosslinked low density polyethylene membranes and crosslinked high density polyethylene membranes.

34. The method according to claim 31 wherein the separation is conducted in a carbon monoxide and hydrogen containing atmosphere where the partial pressures of the carbon monoxide and hydrogen are less than one atmosphere.

35. The method according to claim 31 wherein the separation is conducted at a temperature in the range between about 50° C. to about 145° C.

36. A method for producing higher aldehydes and higher alcohols which comprises:
  (a) hydroformylating an olefinic feedstock with synthesis gas in the presence of a Group VIII noble metal-ligand complex catalyst to form a crude reaction product comprised of an olefin feed, a hydroformylation reaction product and a Group VIII noble metal-ligand complex catalyst;
  (b) removing said Group VIII noble metal-ligand complex catalyst from said crude reaction product by feeding said crude reaction product to a membrane separator which comprises a dense polymeric, nonpolar membrane capable of allowing a substantial portion of said hydroformylation reaction product and unreacted olefin feed to pass therethrough while retaining a substantial portion of said Group VIII noble metal-ligand complex catalyst;
  (c) recovering said hydroformylation reaction product and said unreacted olefin feed as permeate;
  (d) retaining said Group VIII noble metal-ligand complex catalyst as retentate; and
  (e) recycling the retained Group VIII noble metal-ligand complex catalyst to said hydroformylation step (a).

37. The method according to claim 36 wherein the nonpolar membrane is a nonpolar polyolefin membrane.

38. The method according to claim 37 wherein said nonpolar polyolefin membrane is selected from the group consisting of: polypropylene membranes, crosslinked low density polyethylene membranes and crosslinked high density polyethylene membranes.

39. The method according to claim 36 wherein the separation is conducted in a carbon monoxide and hydrogen containing atmosphere where the partial pressures of the carbon monoxide and hydrogen are less than one atmosphere.

40. The method according to claim 36 wherein the separation is conducted at a temperature in the range between about 50° C. to about 145° C.

* * * * *